(12) United States Patent
Hong et al.

(10) Patent No.: US 7,740,844 B2
(45) Date of Patent: Jun. 22, 2010

(54) ANTI-VEGF MONOCLONAL ANTIBODY

(75) Inventors: Keelung Hong, San Francisco, CA (US); Luke S. S. Guo, San Francisco, CA (US); Yun-Long Tseng, Taipei (TW); Hsiu-Li Song, Taipei (TW); Po-Chun Chang, Taipei (TW); Sheue-Fang Shih, Taipei (TW)

(73) Assignees: Taiwan Liposome Co. Ltd, Taipei (TW); TLC Biopharmaceuticals, Inc., San Francisco, CA (US)

(*) Notice: Subject to any disclaimer, the term of this patent is extended or adjusted under 35 U.S.C. 154(b) by 16 days.

(21) Appl. No.: 12/111,606

(22) Filed: Apr. 29, 2008

(65) Prior Publication Data

US 2009/0269336 A1 Oct. 29, 2009

(51) Int. Cl.
- A61K 39/395 (2006.01)
- A61K 39/00 (2006.01)
- C12P 21/08 (2006.01)
- C07K 16/00 (2006.01)
- C07K 16/18 (2006.01)
- C07K 16/22 (2006.01)

(52) U.S. Cl. .............. 424/130.1; 424/133.1; 424/141.1; 424/142.1; 424/145.1; 530/387.1; 530/387.3; 530/388.1; 530/388.15; 530/388.24

(58) Field of Classification Search ................ None
See application file for complete search history.

(56) References Cited

OTHER PUBLICATIONS

Rudikoff et al, Proc Natl Acad Sci USA 79: 1979-1983, 1982.*
Kobrin et al, J Immunology 146: 2017-2020, 1991.*
Barrios et al, J Molecular Recognition 17: 332-338, 2004.*
Aiello, "Vascular Endothelial Growth Factor in Ocular Fluid of Pateitns with Diabetic Retinopathy and Other Retinal Disorders", *The New England Journal of Medicine*, vol. 331:1480-1487, Dec. 1, 1994, No. 22.
Boulton, "VEGF localization in diabetic retinopathy", *Br Ophthalmol* 1998; 82:561-568.
Ferrara, "Vascular Endothelial Growth Factor: Basic Science and Clinical Progress", *Endocrine Reviews* 25(4): 581-611, 2004.
Fuh, "Structure-Function Studies of Two Synthetic Anti-vascular Endothelia Growth Factor Fabs and Comparison with the Avastin™ Fab*", *The Journal of Biological Chemistry* vol. 281, No. 10, pp. 6625-6631, Mar. 10, 2006.
Kim, "Inhibition of vascular endothelial growth factor-induced angiogenesis suppresses tumour growth in vivo", *Letters to Nature* 362: 841-844, Apr. 1993.
Kohler, "Continuous cultures of fuses cells secreting antibody of predefined specificity", *Nature* vol. 256, Aug. 7, 1975, pp. 495-497.
Liang, "Cross-species Vascular Endothelial Growth Factor (VEGF)-blocking Antibodies Completely Inhibit the Growth of Human Tumor Xenografts and Measure the Contribution of Stromal VEGF*", *Journal of Biological Chemistry*, Jan. 13, 2006, vol. 281, No. 2, 951-961.
Morrison, "Chimeric human antibody molecules: Mouse antigen-binding domains with human constant region domains", *Proc. Natl. Acad. Sci. USA*, vol. 81, pp. 6851-6855, Nov. 1984.
Muller, "The crystal structure of vascular endothelial growth factor (VEGF) refined to 1.93 A resolution: multiple copy flexibility and receptor binding", *Structure* Oct. 15, 1997, 5:1325-1338.
Ohno-Matsui, "Novel Mechanism for Age-Related Macular Degneration: An Equilibrium Shift Between the Angiogenesis Factgors VEGF and PEDF", *Journal of Cellular Physiology* 189:323-333 (2001).
Rosenfeld, "Ranibizumab for Neovascular Age-Related Macular Degeneration", *The New England Journal of Medicine*, Oct. 5, 2006, vol. 355 No. 14, 1419-1431.
Takeda, "Construction of chimaeric processed immunoglobulin genes containing mouse variable and human constant region sequences", *Nature* vol. 314, Apr. 4, 1985, pp. 452-454.
Tobe, Targeted Disruption of the FGF2 Gene Does Not Prevent Choroidal Neovascularization ina Murine Model, *American Journal of Pathology*, vol. 153, No. 5, Nov. 1998, pp. 1641-1646.
Wiesmann, "Crystal Structure of the Complex between VEGF and a Receptor-Blocking Peptide", *Biochemistry 1998*, 37, 17765-17772.

* cited by examiner

*Primary Examiner*—Phuong Huynh
(74) *Attorney, Agent, or Firm*—Occhiuti Rohlicek & Tsao LLP (57) ABSTRACT

The present invention provides novel monoclonal antibodies with a high binding affinity to all five isoforms of human VEGF.

15 Claims, 5 Drawing Sheets

```
 3          10          20          30          40          50
MAEGGGQNHHEVVKFMDVYQRSYCHPIETLVD IFQEYPDEIEYIFKPS
  β 1              α 1          β 2       α 2        β 3

60          70          80          90          100
CVPLMRCGGCCNDEGLECVPTEESNITMQIMRIKPHQGQHIGEMSFLQHN
  β 4                  β 5                      β 6

110
KCECRPKKDRARQE
  β 7
```

```
1         10        20        30        40        50
EIQLLQSGPELVKPGASVKISCKASGYSFTGYFMNWVMQSHGRTLEWIGR 60        70        80        90        100
INPYTGETLYNQKFKDKATLTAEISSSTAHMELRSLASDDSAVYFCARRG 110       120
YAGSGGIYSMDSWGPGTSVTVSS
```

FIG. 2A

```
1         10        20        30        40        50
EIVLTQSPAIMSASLGERVTMTCTASSAVSSSYLHWYHQKPGSSPKLWIF 60        70        80        90        100
STSNLASGVPSRFTGSGSGTSYSLTISSVEAEDAATYYCHQYHRSPYTFG

118
AGTKLELN
```

ANTI-VEGF MONOCLONAL ANTIBODY

FIELD OF THE INVENTION

The present invention relates to anti-VEGF monoclonal antibodies.

BACKGROUND OF THE INVENTION

Angiogenesis, i.e., new blood vessel formation, is essential during embryogenesis and occurs directly after the process vasculogenesis [Gilbert et al. (1997) *Developmental biology*, Sunderland (MA): Sinauer]. It also plays a critical role in various pathologic disorders including neoplastic [Folkman et al. (1974) *Adv Cancer Res* 19: 331-58] and certain non-neoplastic diseases such as age-related macular degeneration (AMD), rheumatoid arthritis and diabetic retinopathy [Ohno-Matsui et al. (2001) *J Cell Physiol* 189: 323-333; Aiello et al. (1994) *N Engl J Med* 331: 1480-1487; Boulton et al. (1998) *Br J Opthalmol* 82: 561-568].

Vascular endothelial growth factor (VEGF) is one of the most potent positive regulators in angiogenesis [Ferrara et al. (2004) *Endocr Rev* 25: 581-611]. Blocking the activity of VEGF derived from tumor cells by specific antibodies suppressed tumor growth in mouse models [Kim et al. (1993) *Nature* 362: 841-844; Liang et al. (2006) *J. Biol. Chem.* 281: 951-961]. Bevacizumab, a specific humanized antibody against human VEGF, was approved for treating colorectal cancer patients [Hurwitz et al. (2004) *Clin. Colorectal Cancer* 4: suppl. 2, S62-S68] and Ranibizumab, a recombinant humanized antibody fragment against human VEGF, was also clinically effective for neovascular AMD patients [Rosenfeld et al. (2006) *N Engl J Med* 5; 355(14):1419-31]. It is validated that anti-angiogenesis is a successful approach to arrest tumor growth and improve visual acuity in neovascular AMD through blockade of VEGF.

BRIEF SUMMARY OF THE INVENTION

The present invention is based on the identification of an antibody, i.e., VC300, that specifically binds to amino acid residues $Asn_{100}$ to $Lys_{107}$ in human VEGF (SEQ ID NO:9). This antibody, having an unexpected low $K_d$ value, i.e., $<2\times10^{-9}$ M, neutralizes VEGF activity.

Accordingly, the present invention provides an human VEGF-specific monoclonal antibody that binds to amino acid residues $Asn_{100}$ to $Lys_{107}$ in human VEGF (SEQ ID NO:9) and has a $K_d$ value no more than $2\times10^{-9}$ M. In one example, this monoclonal antibody has a heavy chain variable region comprising one or more amino acid sequences of SEQ ID NOs: 1, 2 and 3, and a light chain variable region comprising one or more amino acid sequences of SEQ ID NOs: 4, 5 and 6. Preferably, the antibody of this invention has a heavy chain variable region including all of the amino acid sequences SEQ ID NOs:1, 2, and 3 (e.g., having the amino acid sequence of SEQ ID NO:10) and a light chain variable region including all of the amino acid sequences SEQ ID NOs:4, 5, and 6 (e.g., having the amino acid sequence of SEQ ID NO:11). The term "monoclonal antibody" used herein refers to an antibody composition having a homogenous antibody population, i.e., a homogeneous population consisting of a whole immunoglubolin or a fragment thereof.

In one example, the monoclonal antibody of this invention is a whole immunoglobulin. In another example, the antibody is a fragment of a whole immunoglobulin that possesses antigen-binding activity, e.g., Fab, Fab', $F(ab)_2$, or $F(ab')_2$ fragment. The monoclonal antibody of this invention also can be a non-naturally occurring molecule, e.g., a chimeric antibody, a humanized antibody, or a single-chain antibody. A chimeric antibody is a molecule in which different portions are derived from different animal species, such as those having a variable region derived from a murine monoclonal antibody and a human immunoglobulin constant region. A humanized antibody is a non-human antibody, in which the frame regions (FRs) of its $V_H$ and $V_L$ are replaced with FRs of a human antibody. A single-chain antibody is a single polypeptide that contains both a heavy chain variable region and a light chain variable region.

Also within the scope of this invention is use of any of the monoclonal antibodies described above for treating a VEGF-related angiogenic disease, e.g., cancer, age-related macular degeneration (AMD), rheumatoid arthritis and diabetic retinopathy, by administering to a subject in need of the treatment an therapeutically effective amount of the antibody.

The term "treating" as used herein refers to the application or administration of a composition including active agents to a subject, who has a VEGF-related angiogenic disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent which, upon administration with one or more other active agents to a subject in need thereof, is required to confer therapeutic effect on the subject. Effective amounts vary, as recognized by those skilled in the art, depending on route of administration, excipient usage, and the co-usage with other active agents.

The monoclonal antibody of this invention is also useful for the manufacture of a medicament for the treatment of a VEGF-related angiogenic disease.

The details of one or more embodiments of the invention are set forth in the description below. Other features, objects, and advantages of the invention will be apparent from the description, and from the claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

The following abbreviations are used throughout the present invention:
AMD=age-related macular degeneration;
CDR=complementary determining regions;
CNV=choroidal neovascularization;
HUVEC=human umbilical vein endothelial cells;
mAb=monoclonal antibody;
VEGF=vascular endothelial growth factor.

Unless defined otherwise, all technical and scientific terms used herein have the same meanings as those commonly understood to one of ordinary skill in the art to which this invention pertains.

The term "$K_d$", as used herein, is intended to refer to the dissociation constant or the "off" rate divided by the "on" rate, of a particular antibody-antigen interaction. For purposes of the present invention $K_d$ was determined as shown in Example 4.

Figure 1A:
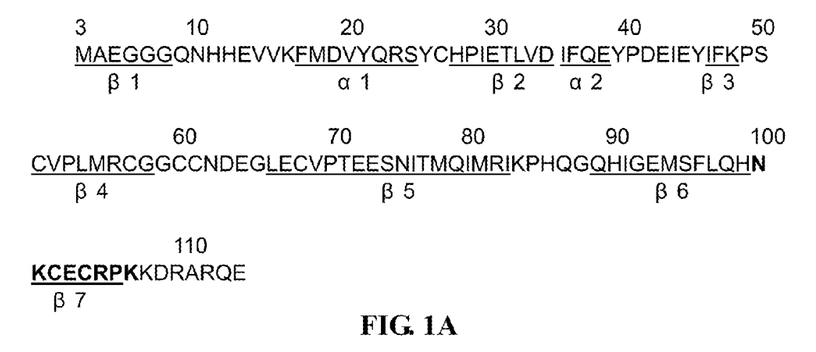
FIG. 1A shows the sequence of $VEGF_{3-114}$ (SEQ ID NO: 8), wherein α-helices and β-strands are underlined and labeled according to Wiesmann et al [Wiesmann et al. (1998) *Biochemistry* 37:17765-17772], and the binding epitope for VC300 mAb is shown in bold.

As used herein, the term "VEGF" or "human VEGF" refers to the full length human vascular endothelial cell growth factor, which has an amino acid sequence of SEQ ID NO: 9 [Leung et al. (1989) Science 246:1306-1309], or isoforms or fragments thereof, which functions as a platelet-derived growth factor. As mentioned in Ferrara et al., five isoforms were produced from the full-length VEGF by alternative splicing [Ferrara (1999) J Mol Med 77: 527-543]. According to the structural and functional studies, it was demonstrated that the receptor binding domain of VEGF was ranging from the amino acid residues $Gly_8$ to $Asp_{109}$ of the full length VEGF [Muller et al. (1997) Structure 5: 1325-1338; Fuh et al., (2006) J. Biol. Chem. 281: 6625-6631]. In the present invention, a recombinant $VEGF_{3-114}$ (SEQ ID NO: 8; FIG. 1A) was used in mice immunization and the anti-VEGF monoclonal antibody were obtained.

The present invention provides an anti-VEGF monoclonal antibody that binds to amino acid residues $Asn_{100}$ to $Lys_{107}$ of human VEGF (SEQ ID NO:9), a common epitope in all five human VEGF isoforms, with a $K_d$ value of no more than about $2\times10^{-9}$ M. While binding to VEGF, this anti-VEGF antibody neutralizes VEGF, thereby inhibiting antiogenesis.

To produce an antibody of this invention, a peptide containing the epitope described above can be coupled to a carrier protein, such as KLH, mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and Corynebacterium parvum.

Polyclonal antibodies specific to $Asn_{100}$ to $Lys_{107}$ of human VEGF are present in the sera of the immunized subjects as described above. Monoclonal antibodies can then be prepared by, e.g., standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; Kosbor et al, (1983), the human B-cell hybridoma technique, Immunol Today 4, 72; Cole et al. (1983) Proc. Natl. Acad. Sci. USA 80, 2026; and Cole et al. (1983), the EBV-hybridoma technique (Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

Once a hybridoma cell line has been established, the affinity of the monoclonal antibody produced thereby to $Asn_{100}$ to $Lys_{107}$ of human VEGF can be determined by methods known in the art and those having $K_d$ values no more than $2\times10^{-9}$ M can be identified.

Monoclonal antibodies produced by a hybridoma cell line are whole immunoglobulin molecules. These immunoglobulin molecules can be treated by, e.g., enzymatic cleavage, to produce functional fragments of the immunoglobulin, i.e., a fragment that retains antigen-binding activity. Such functional fragments include Fab, Fab', $F(ab)_2$, or $F(ab')_2$ fragments. The term "Fab fragment" used herein refers to an antibody fragment containing the constant domain of the light chain and the first constant domain (CH1) of the heavy chain. The term "Fab' fragment" refers to an antibody fragment, differing from Fab fragments by the addition of a few residues at the carboxyl terminus of the heavy chain CH1 domain including one or more cysteine(s) from the antibody hinge region. The term "$F(ab')_2$ fragment" refers to an antibody fragment originally produced as pairs of Fab' fragments which has hinge cysteines between them. Such forms can be prepared by any known technique, such as, but not limited to, enzymatic cleavage, peptide synthesis, or recombinant expression.

The anti-VEGF antibody of this invention can also be prepared by recombinant technology. An example follows. Genes encoding the heavy chain variable region ($V_H$) and the light chain variable region ($V_L$) of an antibody are cloned from the hydridoma cells that produce the antibody. The complementarity-determining regions (CDRs) and frame regions (FRs) of both the heavy chain variable region and the light chain variable region can be determined based on the amino acid sequences of its $V_H$ and $V_L$. See www.bioinf.org.uk/abs. The $V_H$ and $V_L$ polypeptides can then be expressed in a host cell and reconstituted in vivo or in vitro to form an antibody of this invention.

Techniques for preparing non-naturally occurring antibody molecules, e.g., chimeric antibody, humanized antibody, or single-chain antibody, are also well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

In one example, the monoclonal antibody of the present invention has a heavy chain variable region comprising one or more of the following $V_H$-CDRs, and a light chain variable region comprising one or more of the following $V_L$-CDRs:

| | | |
|---|---|---|
| $V_H$-CDR1: | GYFMN; | (SEQ ID NO: 1) |
| $V_H$-CDR2: | RINPYTGETLYNQKFKD; | (SEQ ID NO: 2) |
| $V_H$-CDR3: | RGYAGSGGIYSMDS; | (SEQ ID NO: 3) |
| $V_L$-CDR1: | TASSAVSSSYLH; | (SEQ ID NO: 4) |
| $V_L$-CDR2: | STSNLAS; | (SEQ ID NO: 5) |
| $V_L$-CDR3: | HQYHRSPYT. | (SEQ ID NO: 6) |

In addition, it is possible to prepare variants of the antibody of the present invention with high affinity to VEGF by standard molecular biological techniques. The variant refers herein to a molecule which differs in amino acid sequence from the parent amino acid sequence by addition, deletion and/or substitution of one or more amino acid residue(s) in one or more CDR(s) of the parent antibody. The amino acid sequence of the variant's CDR(s) usually has at least 75% (e.g., 80%, 85%, 90%, 95%, 98%, or 99%) sequence identity to the parent antibody's CDR(s).

The monoclonal antibody of the present invention can be incorporated into pharmaceutical compositions suitable for administration to a subject. Typically, the pharmaceutical composition comprises a therapeutically effective amount of the monoclonal antibody of the invention, and a pharmaceutically acceptable diluent, carrier, and/or excipient. "Acceptable" means that the carrier must be compatible with the active ingredient of the composition (and preferably, capable of stabilizing the active ingredient) and not deleterious to the subject to be treated. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate.

The monoclonal antibody of the present invention can also be entrapped in a microcapsule. For example, the monoclonal antibody may be prepared by coacervation techniques or by interfacial polymerization in a drug delivery system such as liposomes and nano-particles through any standard or commonly used in the art.

The pharmaceutical composition described above is useful in treating various VEGF-related angiogenic diseases. The VEGF-related angiogenic disease may include, but not be limited to, AMD, rheumatoid arthritis and diabetic retinopathy. It can be administered to a subject in need of the treatment via a suitable route, e.g., intravenous, intraperitoneal, subcutaneous, pulmonary, transdermal, intramuscular, intranasal, buccal, sublingual, or suppository administration.

In a preferred embodiment of the invention, the monoclonal antibody is formulated into a pharmaceutical composition, such as a solution suitable for intravitreal injection.

The effectiveness of the monoclonal antibody of the invention in preventing or treating disease may be improved by administering the antibody serially or in combination with another agent that is effective for those purposes. Such other agents may be present in the composition being administered or may be administered separately. Also, the antibody is suitably administered serially or in combination with radiological treatments, whether involving irradiation or administration of radioactive substances.

Non-therapeutic uses of the monoclonal antibody of the invention include but not are limited to affinity purification and diagnostic assays.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Generation of Anti-VEGF Monoclonal Antibody

The cDNA encoding $VEGF_{3-114}$ (SEQ ID NO: 7) was cloned and expressed in a prokaryotic system. The $VEGF_{3-114}$ was purified to homogeneity for mice immunization. Monoclonal antibody were generated according to Kohler's method [Kohler (1975) *Nature*, 256: 495]. In brief, six-week-old BALB/c male mice were immunized four times with the recombinant $VEGF_{3-114}$. The lymphocytes were harvested and fused with myeloma cells by polyethylene glycol 1500 (Roche Diagnostics GmbH, Mannheim, Germany) to generate hybridoma cells. The hybridoma cells were seeded and grown in a selected culture medium containing hypoxanthine, aminopterin and thymidine (Invitrogen Corporation, Carlsbad, Calif.) to allow the growth of hypoxanthine guanine phosphoribosyl transferase-positive cells. The culture media were collected and screened for the presence of the antibodies reacting with the $VEGF_{3-114}$ antigen by ELISA. Limited dilution method was applied to select the antibody producing positive clones. After several rounds of selection, a clone which produced a high level of anti-VEGF antibodies was obtained and designated as VC300.

Example 2

Epitope Mapping of VC300 mAB

Figure 1B:
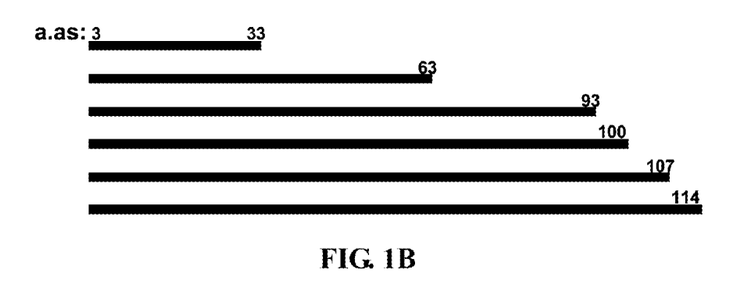
FIG. 1B shows various truncated VEGF fragments.

To elucidate the binding epitope of VC300 mAb, the $VEGF_{3-114}$ (SEQ ID NO: 8) and five VEGF fragments, $VEGF_{3-33}$, $VEGF_{3-63}$, $VEGF_{3-93}$, $VEGF_{3-100}$, and $VEGF_{3-107}$ (see FIG. 1B), were used in the mapping. Nucleotide sequences of all these constructs were verified by DNA sequencing. Expression profiles of fusion proteins were analyzed by 12.5% SDS-PAGE and Western blot analysis with anti-penta-His monoclonal antibody (Qiagen, Valencia, Calif.). The lysates were used in verification of the binding epitope of VC300 mAb.

*E. coli* cells containing various truncated fragments of VEGF cDNA in expression vector were induced to express recombinant proteins with 0.4 mM isopropyl-β-D-thiogalactopyranoside (IPTG, Sigma-Aldrich, St. Louis, Mo.) at 37° C. for 3 h and the cells were harvested by centrifugation at 10,000 rpm for 2 min. The cell pellets were suspended and lysed with protein sample buffer, boiled for 10 min and analyzed by a 12.5% SDS-PAGE. For Western blot analysis, the gels were electroblotted onto PVDF membranes and the membranes were blocked with 5% skim milk in phosphate-buffered saline, pH 7.4 containing 0.05% Tween 20 at RT for 1 h, probed with a 1:1000 dilution of anti-penta-His monoclonal antibody or VC300 mAb followed by reaction with HRP-conjugated goat anti-mouse immunoglobulin (Chemicon Int., Temecula, Calif.). The binding reaction was detected by the addition of the diaminobenzidine (Sigma-Aldrich, St. Louis, Mo.) color development reagent, 0.05% diaminobenzidine, 0.005% hydrogen peroxide in 0.1 M Tris-HCl, pH 7.4.

Figure 1C:
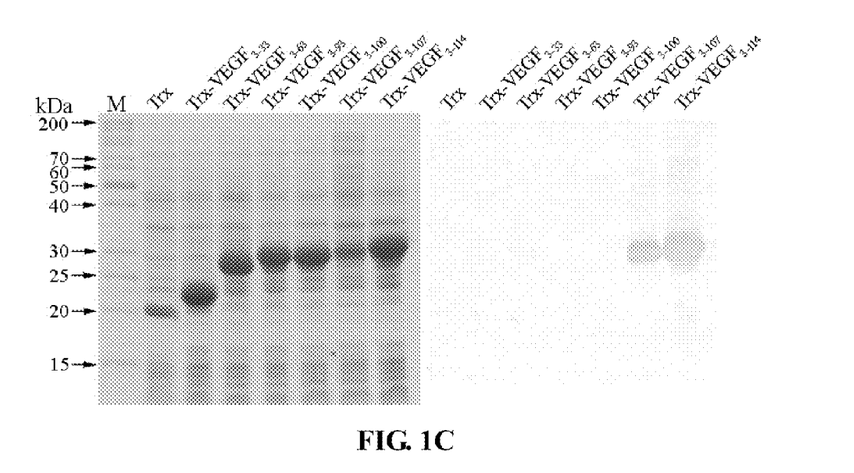
FIG. 1C shows expression of the VEGF fragments in *E. coli* as determined by SDS-PAGE (left panel, M=markers), and verification of the binding epitope of VC300 mAb by Western blot analysis (right panel).

It was expected that the epitope would span a continuous region on the antigen since the VC300 mAb was capable of recognizing $VEGF_{3-114}$. Under this assumption, five truncated fragments of VEGF were used in verification of the binding epitope. All of the fragments of VEGF were expressed well in *E. coli* cells as revealed by SDS-PAGE (FIG. 1C, left panel) and Western blot analyses with anti-penta-His monoclonal antibody (data not shown). In FIG. 1C (right panel), the results show that the VC300 mAb had no reaction to four fragments, $VEGF_{3-33}$, $VEGF_{3-63}$, $VEGF_{3-93}$, $VEGF_{3-100}$ except for $VEGF_{3-107}$ and $VEGF_{3-114}$. These results indicate that the amino acid residues $Asn_{100}$ to $Lys_{107}$ of the full length VEGF (SEQ ID NO: 9) contribute to the binding epitope on VEGF recognized by the VC300 mAb.

Example 3

Identification of VC300 mAb cDNA

Figure 2A:
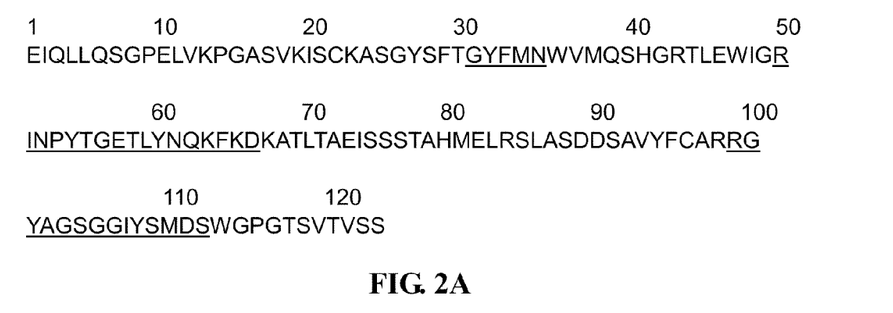
FIGS. 2A and 2B show the amino acid sequences of the VC300 mAb in the heavy chain variable region (SEQ ID NO: 10) and light chain variable region (SEQ ID NO: 11), respectively. The CDRs were determined based on the analytic method developed by Kabat et al. [(1991) Sequences of Proteins of Immunological Interest, Fifth Edition. NIH Publication No. 1991; 91-3234] and are underlined.
Figure 2B:
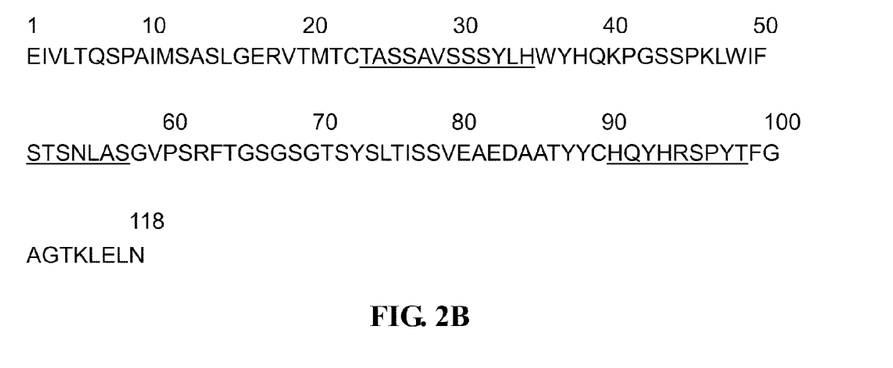

Total mRNA was extracted from $5\times10^6$ hybridoma cells producing VC300 mAb by an mRNA purification kit, Oligotex Maxi Kit (Qiagen, Valencia, Calif.). The cDNA was synthesized using RT-PCR with the designed primers according to Amersdorfer et al. (1997) *Infect Immun.*, 65(9): 3743-3752. The resulting cDNA was subcloned into the TA vector (Invitrogen, CA, USA) and sequenced. The deduced amino acid sequences of $V_H$ and $V_L$ are depicted in FIGS. 2A and 2B. In the $V_H$ sequence, it contains the heavy chain hypervariable regions, CDR1, CDR2 and CDR3, and their sequences are GYFMN (SEQ ID NO: 1), RINPYTGETLYNQKFKD (SEQ ID NO: 2) and RGYAGSGGIYSMDS (SEQ ID NO: 3), respectively. In the $V_L$ sequence, the sequences of CDR1, CDR2 and CDR3 are TASSAVSSSYLH (SEQ ID NO: 4), STSNLAS (SEQ ID NO: 4), and HQYHRSPYT (SEQ ID NO: 6), respectively.

The amino acid sequences of $V_H$ and $V_L$ fragments, CDRs especially, were blasted by the NCBI Database and the data indicate that these are novel CDRs in the $V_H$ and $V_L$ of mouse monoclonal antibody. These data indicate that the VC300 mAb is a novel anti-VEGF monoclonal antibody and is valuable for clinical applications.

Example 4

Preparation and Characterization of VC300 mAb

The VC300 mAb was purified from mice ascites by ammonium sulfate precipitation and CM Sepharsoe chromatography (GE Healthcare, Piscataway, N.J.). The purified VC300 mAb was analyzed by 7.5% SDS-PAGE and the protein concentration was quantitated by the absorbance at 280 nm. Isotype determination of VC300 mAb was carried out by a monoclonal antibody isotyping kit I obtained from PIERCE (Rockford, Ill., USA). The dissociation constant ($K_d$) of antigen-antibody interaction was determined by competitive ELISA [Lin et al., (1997) *Anal. Biochem.*, 254: 9-17]. In brief, the antigen, $VEGF_{3-114}$, at various concentrations was incubated with the antibody, VC300 mAb at 4° C. for overnight to reach equilibrium. The mixtures were transferred to the wells coated with 3 μg/ml of $VEGF_{3-114}$ and incubated at room temperature for 1 h. The amount of VC300 mAb bound to the well was revealed by adding goat anti-mouse conjugated HRP (horseradish peroxidase), followed by incubation with 2,2-Azino-bis-3ethylbenz-thiazoline-6 sulphonic acid (ABT, Sigma-Aldrich, St. Louis, Mo.). Absorbance at 450 nm was measured and the $K_d$ value was calculated as described previously.

Figure 3:
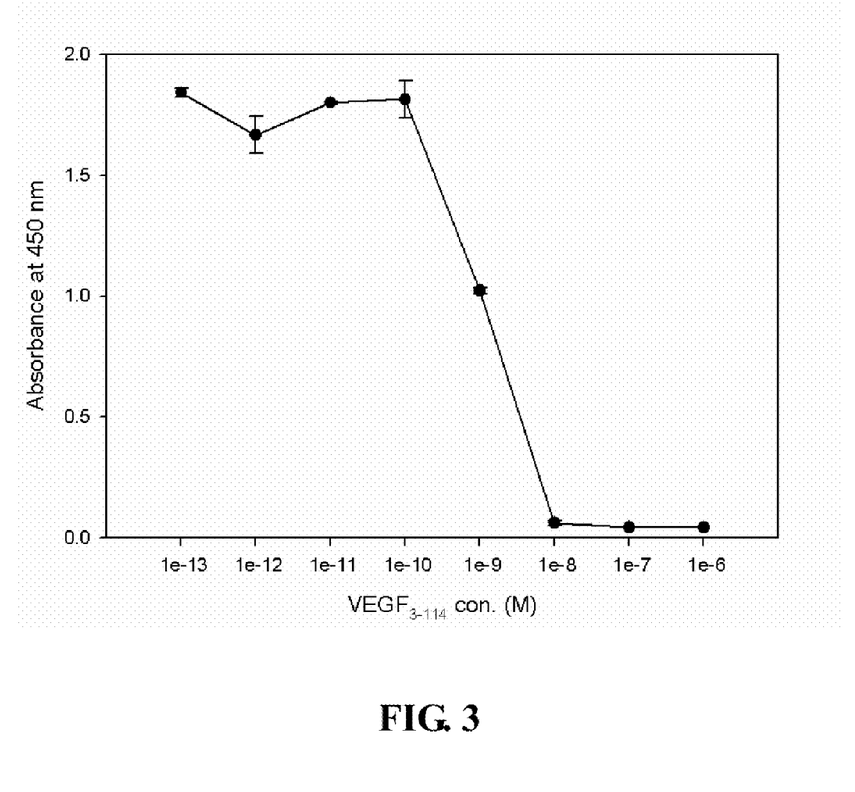
FIG. 3 shows the binding affinity of VC300 mAb to human $VEGF_{3-114}$.

The isotype of VC300 mAb was determined to be IgG1 (data not shown) and the $K_d$ is about $2\times10^{-9}$ M as shown in FIG. 3. In terms of the high affinity to VEGF, VC300 mAb could effectively attenuate growth of new blood vessel induced by VEGF in vitro and in vivo.

Example 5

Neutralizing Activity of VC300 mAB In Vitro

To evaluate the neutralizing activity of VC300 mAb in vitro, the HUVEC proliferation assay was performed. The HUVECs (H-UV001) were purchased from Bioresource Collection and Research Center, Hsinchu, Taiwan and cultured in gelatin-coated flasks in M199 medium (Invitrogen Corporation, Carlsbad, Calif.) containing 20% (v/v) fetal bovine serum (FBS, Hyclone, Utah, USA), 3 μg/ml endothelial cell growth supplement (ECGS, Sigma-Aldrich, St. Louis, Mo.), 5 IU/ml heparin (Sigma-Aldrich, St. Louis, Mo.), 1 mM pyruvate, 2 mM glutamine, 100 U/ml penicillin and 0.1 mg/ml streptomycin at 37° C. and 5% $CO_2$. For the proliferation assay, HUVECs were seeded at the density of 4000 cells/well in M199 medium containing 1.5% (v/v) FBS, 5 IU/ml heparin, 1 mM pyruvate, 2 mM glutamine, 100 U/ml penicillin and 0.1 mg/ml streptomycin, and incubated at 37° C. overnight. The HUVECs were stimulated for 32 h with 13.6 ng/ml $VEGF_{3-114}$ in the presence of increasing concentrations of VC300 mAb. BrdU was then added and the HUVECs were incubated for additional 16 h. The incorporated BrdU was measured with BrdU Cell Proliferation Assay purchased from Calbiochem (San Diego, Calif.).

Figure 4:
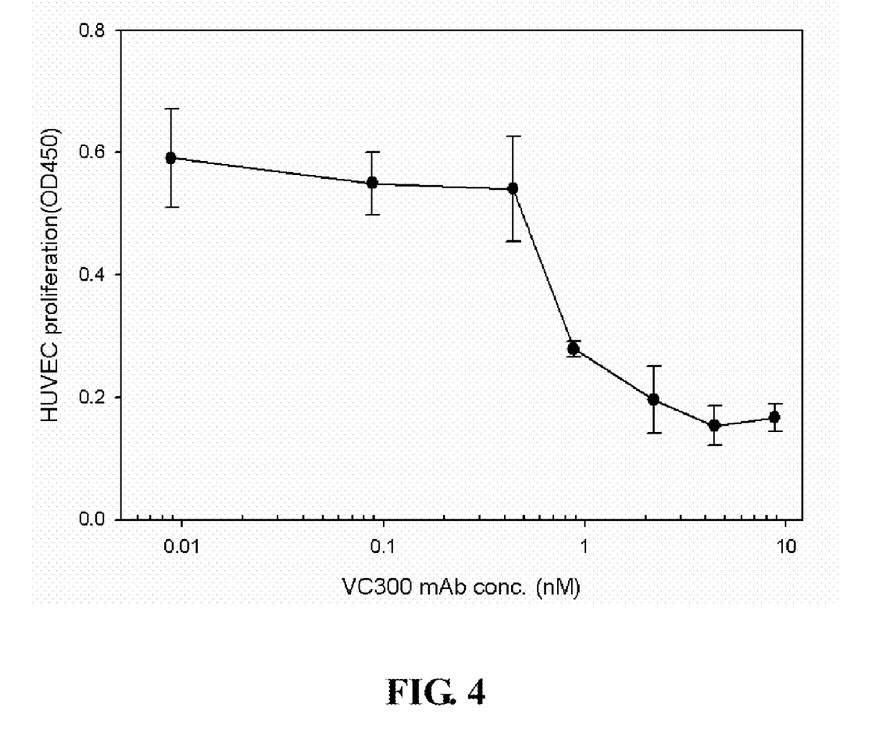
FIG. 4 depicts the effect of VC300 mAb on the inhibition of VEGF-induced HUVEC proliferation.

The HUVEC proliferation with 13.6 ng/ml of VEGF treatment increases about 3-fold at 48 h compared with the VEGF-free control. The effect of VEGF was reduced to baseline levels in the presence of above 2 nM anti-VEGF monoclonal antibody, VC300 mAb. As shown in FIG. 4, the HUVEC proliferation curve was plotted and the value of $IC_{50}$ is about 1 nM. These data suggest that the VC300 mAb is able to specifically bind to VEGF and neutralize VEGF activity.

Example 6

Neutralizing Activity of VC300 mAB In Vivo

CNV was generated by a previously described technique with modifications [To be et al., (1998) *Am J. Pathol,* 153: 1641-1646]. All experiments were conducted in accordance with the Association for Research in Vision and Opthalmology (ARVO) statement for the Use of Animals in Ophthalmic and Vision Research. Briefly, Brown-Norway (BN) rats were anesthetized with intramuscular injection of 0.15 ml/kg of an equal-volume mixture of 2% lidocaine (Xylocaine; Astra, Astra Södertälje, Sweden) and 50 mg/mL ketamine (Ketalar; Parke-Davis, Morris Plains, N.J.). After anesthetizing, the right pupils were dilated with 1% tropicamide (1% Mydriacyl; Alcon Laboratories). A small piece of transparent sheet (3M, Minneapolis, Minn.) approximately 3 mm in diameter was attached to the cornea by sodium hyaluronidase (Healon; Pharmacia and Upjohn) to serve as a contact lens. Krypton laser (Novus Omni; Coherent, Palo Alto, Calif.) irradiation was delivered through a slit lamp (Carl Zeiss, Oberkochen, Germany). Laser parameters used were as follows: spot size=100 mm, power=120 to 160 mW, and exposure duration=0.1 second. An attempt was made to break Bruch's membrane, as clinically evidenced by central bubble formation, with or without intra-retinal or choroidal hemorrhage. Four lesions were created between the major retinal vessels in right fundus. The CNV lesions were examined on day 14 by ophthalmicroscopy, fundus photography, and conventional fluorescein angiography (FAG) with a digital fundus camera (Retinal Angiography; Heidelberg Engineering, Heidelberg, Germany). After generation of lesions, lesion sites were treated with saline or VC300 mAb and the rat retina was re-examined by fluorescein angiography. Fluorescein angiograms of rat retina were performed 2 weeks after argon-laser induction of CNV and the fluorescein leakage at the site of the initial laser injury was examined.

Figure 5:
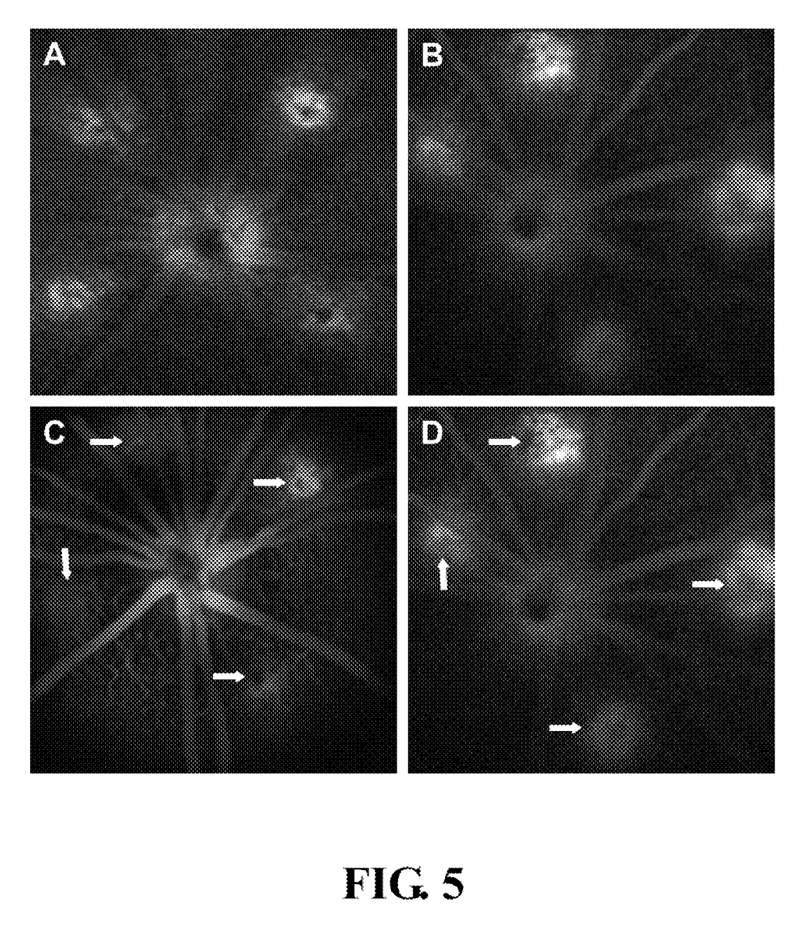
FIG. 5 depicts the effect of VC300 mAb on attenuating the extent of laser photocoagulation-induced CNV in a rat model. The fluorescein angiogram of rat retina 2 weeks after argon-laser induction of CNV in A (right eye) and B (left eye) followed by different treatments for additional one week shown in C (treated with VC300 mAb) and D (saline control). Arrows represent areas of fluorescein leakage at the site of the laser injury.

As shown in FIGS. 5A and 5B, the intensity of fluorescein leakage indicates the creation of CNV lesions is successful in right and left eyes. After the induction of CNV for two weeks, lesion sites were treated with or without VC300 mAb, and the fluorescein angiograms of rat retina were analyzed. The data show that the VC300 mAb effectively attenuates the extent of fluorescein leakage as shown in FIGS. 5C (VC300 mAb treatment) and 5D (saline control). These results indicate that the VC300 mAb is capable of neutralizing VEGF to attenuate the angiogenesis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

---

We claim:

1. An anti-human vascular endothelial growth factor (VEGF) monoclonal antibody or a binding fragment thereof, wherein said antibody comprises a heavy chain variable region containing the CDR amino acid sequences of SEQ ID NOs: 1, 2 and 3 and a light chain variable region containing the CDR amino acid sequences of SEQ ID NOs: 4, 5 and 6.

2. The monoclonal antibody according to claim 1, wherein said heavy chain variable region comprising the amino acid sequence of SEQ ID NO:10 and said light chain variable region comprising the amino acid sequence of SEQ ID NO:11.

3. The monoclonal antibody according to claim 1, wherein said binding fragment is a Fab, Fab', F(ab)$_2$, or F(ab')$_2$.

4. The monoclonal antibody according to claim 2, wherein said binding fragment thereof is selected from the group consisting of Fab, Fab', F(ab)$_2$, and F(ab')2.

5. The monoclonal antibody according to claim 2, wherein said antibody is a humanized antibody.

6. The monoclonal antibody according to claim 1, wherein said antibody is a humanized antibody.

7. A method for treating a VEGF-related angiogenic disease, comprising administering to a subject in need thereof a therapeutically effective amount of the monoclonal antibody or binding fragment thereof according to claim 1 wherein the VEGF-related angiogenic disease is selected from the group consisting of cancer, age-related macular degeneration (AMD), rheumatoid arthritis, and diabetic retinopathy.

8. The method according to claim 7, wherein said VEGF-related angiogenic disease is AMD.

9. The method according to claim 7, wherein the binding fragment thereof is selected from the group consisting of Fab, Fab', F(ab)$_2$, and F(ab')$_2$.

10. The method according to claim 7, wherein the heavy chain variable region comprising the amino acid sequence of SEQ ID NO:10 and the light chain variable region comprising the amino acid sequence of SEQ ID NO:11.

11. The method according to claim 7, wherein the antibody is a humanized antibody.

12. The method according to claim 10, wherein the antibody is a humanized antibody.

13. The method according to claim 10, wherein the VEGF-related angiogenic disease is selected from the group consisting of cancer, AMD, rheumatoid arthritis and diabetic retinopathy.

14. The method according to claim 13, wherein the VEGF-related angiogenic disease is AMD.

15. The method according to claim 10, wherein the binding fragment thereof is selected from the group consisting of Fab, Fab', F(ab)$_2$, and F(ab')$_2$.

* * * * *

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: complementarity determining region

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: complementarity determining region

<400> SEQUENCE: 2

Arg Ile Asn Pro Tyr Thr Gly Glu Thr Leu Tyr Asn Gln Lys Phe Lys
1               5                   10                  15

Asp

<210> SEQ ID NO 3
<211> LENGTH: 14
<212> TYPE: PRT
<213> ORGANISM: Artificial Sequence
<220> FEATURE:
<223> OTHER INFORMATION: complementarity determining region

<400> SEQUENCE: 3

Arg Gly Tyr Ala Gly Ser Gly Gly Ile Tyr Ser Met Asp Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: complementarity determining region
```

<400> SEQUENCE: 4

Thr Ala Ser Ser Ala Val Ser Ser Tyr Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: complementarity determining region

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: complementarity determining region

<400> SEQUENCE: 6

His Gln Tyr His Arg Ser Pro Tyr Thr
1               5

<210> SEQ ID NO 7
<211> LENGTH: 336
<212> TYPE: DNA
<213> ORGANISM: Artificial Sequence
<220> FEATURE:
<223> OTHER INFORMATION: fragment of recombinant human VEGF
<220> FEATURE:
<221> NAME/KEY: CDS
<222> LOCATION: (1)..(336)

<400> SEQUENCE: 7

```
atg gca gaa gga gga ggg cag aat cat cac gaa gtg gtg aag ttc atg      48
Met Ala Glu Gly Gly Gly Gln Asn His His Glu Val Val Lys Phe Met
1               5                   10                  15 gat gtc tat cag cgc agc tac tgc cat cca atc gag acc ctg gtg gac      96
Asp Val Tyr Gln Arg Ser Tyr Cys His Pro Ile Glu Thr Leu Val Asp
                20                  25                  30 atc ttc cag gag tac cct gat gag atc gag tac atc ttc aag cca tcc     144
Ile Phe Gln Glu Tyr Pro Asp Glu Ile Glu Tyr Ile Phe Lys Pro Ser
            35                  40                  45 tgt gtg ccc ctg atg cga tgc ggg ggc tgc tgc aat gac gag ggc ctg     192
Cys Val Pro Leu Met Arg Cys Gly Gly Cys Cys Asn Asp Glu Gly Leu
        50                  55                  60 gag tgt gtg ccc act gag gag tcc aac atc acc atg cag att atg cgg     240
Glu Cys Val Pro Thr Glu Glu Ser Asn Ile Thr Met Gln Ile Met Arg
65                  70                  75                  80 atc aaa cct cac caa ggc cag cac ata gga gag atg agc ttc cta cag     288
Ile Lys Pro His Gln Gly Gln His Ile Gly Glu Met Ser Phe Leu Gln
                85                  90                  95 cac aac aaa tgt gaa tgc aga cca aag aaa gat aga gca aga caa gaa     336
His Asn Lys Cys Glu Cys Arg Pro Lys Lys Asp Arg Ala Arg Gln Glu
            100                 105                 110
```

<210> SEQ ID NO 8
<211> LENGTH: 112
<212> TYPE: PRT
<213> ORGANISM: Artificial Sequence
<220> FEATURE:

<223> OTHER INFORMATION: Synthetic Construct

<400> SEQUENCE: 8

Met Ala Glu Gly Gly Gln Asn His His Glu Val Val Lys Phe Met
1               5                   10                  15

Asp Val Tyr Gln Arg Ser Tyr Cys His Pro Ile Glu Thr Leu Val Asp
            20                  25                  30

Ile Phe Gln Glu Tyr Pro Asp Glu Ile Glu Tyr Ile Phe Lys Pro Ser
        35                  40                  45

Cys Val Pro Leu Met Arg Cys Gly Gly Cys Cys Asn Asp Glu Gly Leu
50                  55                  60

Glu Cys Val Pro Thr Glu Glu Ser Asn Ile Thr Met Gln Ile Met Arg
65                  70                  75                  80

Ile Lys Pro His Gln Gly Gln His Ile Gly Glu Met Ser Phe Leu Gln
                85                  90                  95

His Asn Lys Cys Glu Cys Arg Pro Lys Lys Asp Arg Ala Arg Gln Glu
            100                 105                 110

<210> SEQ ID NO 9
<211> LENGTH: 165
<212> TYPE: PRT
<213> ORGANISM: Homo sapiens
<300> PUBLICATION INFORMATION:
<308> DATABASE ACCESSION NUMBER: GenBank AAA35789
<309> DATABASE ENTRY DATE: 1993-04-27
<313> RELEVANT RESIDUES IN SEQ ID NO: (1)..(165)

<400> SEQUENCE: 9

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 10
<211> LENGTH: 123
<212> TYPE: PRT
<213> ORGANISM: Artificial Sequence
<220> FEATURE:
<223> OTHER INFORMATION: recombinant antibody heavy chain variable
      region -continued

```
<400> SEQUENCE: 10

Glu Ile Gln Leu Leu Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Met Gln Ser His Gly Arg Thr Leu Glu Trp Ile
        35                  40                  45

Gly Arg Ile Asn Pro Tyr Thr Gly Glu Thr Leu Tyr Asn Gln Lys Phe
    50                  55                  60

Lys Asp Lys Ala Thr Leu Thr Ala Glu Ile Ser Ser Ser Thr Ala His
65                  70                  75                  80

Met Glu Leu Arg Ser Leu Ala Ser Asp Asp Ser Ala Val Tyr Phe Cys
                85                  90                  95

Ala Arg Arg Gly Tyr Ala Gly Ser Gly Gly Ile Tyr Ser Met Asp Ser
                100                 105                 110

Trp Gly Pro Gly Thr Ser Val Thr Val Ser Ser
        115                 120

<210> SEQ ID NO 11
<211> LENGTH: 108
<212> TYPE: PRT
<213> ORGANISM: Artificial Sequence
<220> FEATURE:
<223> OTHER INFORMATION: recombinant antibody light chain variable
      region

<400> SEQUENCE: 11

Glu Ile Val Leu Thr Gln Ser Pro Ala Ile Met Ser Ala Ser Leu Gly
1               5                   10                  15

Glu Arg Val Thr Met Thr Cys Thr Ala Ser Ser Ala Val Ser Ser Ser
            20                  25                  30

Tyr Leu His Trp Tyr His Gln Lys Pro Gly Ser Ser Pro Lys Leu Trp
        35                  40                  45

Ile Phe Ser Thr Ser Asn Leu Ala Ser Gly Val Pro Ser Arg Phe Thr
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys His Gln Tyr His Arg Ser Pro
                85                  90                  95

Tyr Thr Phe Gly Ala Gly Thr Lys Leu Glu Leu Asn
                100                 105
```